United States Patent [19]
Johnson et al.

[11] Patent Number: 6,159,743
[45] Date of Patent: Dec. 12, 2000

[54] METHOD AND APPARATUS FOR TESTING SURFACES

[76] Inventors: James R. Johnson, 2131 N. Longmore St., Chandler, Ariz. 85224; Jerry J. Colahan, 1127 E. Millett, Mesa, Ariz. 85204

[21] Appl. No.: 09/268,481

[22] Filed: Mar. 16, 1999

Related U.S. Application Data

[60] Provisional application No. 60/078,293, Mar. 17, 1998.
[51] Int. Cl.[7] .................................................. G01N 33/48
[52] U.S. Cl. ......................... 436/174; 436/177; 422/61; 422/99; 422/102
[58] Field of Search ..................................... 436/174, 178, 436/177; 422/58, 61, 99, 103, 104; 220/9.1–9.3, 480; 206/407, 813

[56] References Cited

U.S. PATENT DOCUMENTS

| | | | |
|---|---|---|---|
| 5,069,228 | 12/1991 | Sorkin | 128/844 |
| 5,186,900 | 2/1993 | Jensen et al. | 422/104 |
| 5,552,320 | 9/1996 | Smith | 435/287.4 |

*Primary Examiner*—Lyle A. Alexander
*Attorney, Agent, or Firm*—Parsons & Goltry; Robert A. Parsons; Michael W. Goltry

[57] ABSTRACT

A test kit for testing substrates for soluble salts including a test sleeve, a pre-measured volume of solvent solution, and a soluble salt measuring device. The test sleeve includes a generally tubular body with a closed end and an open end. The open end includes a flange defining an aperture, and an attachment member coupled to the flange for removably securing the testing sleeve to a substrate.

11 Claims, 2 Drawing Sheets

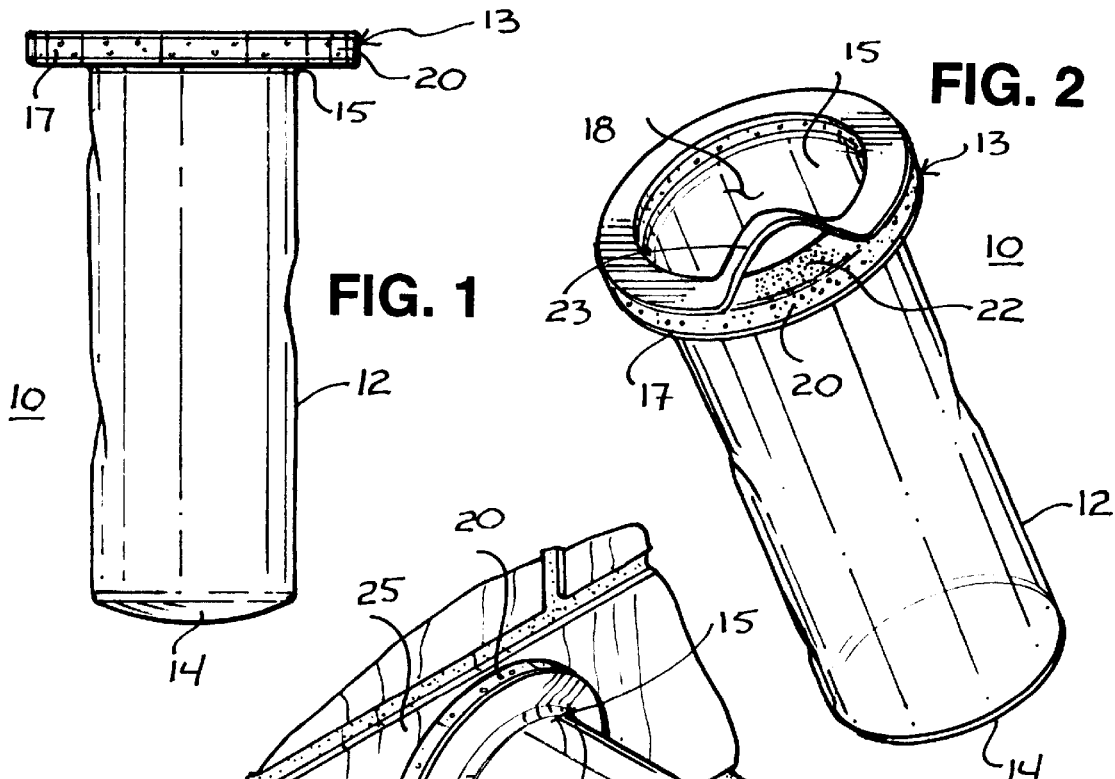
FIG. 1
FIG. 2
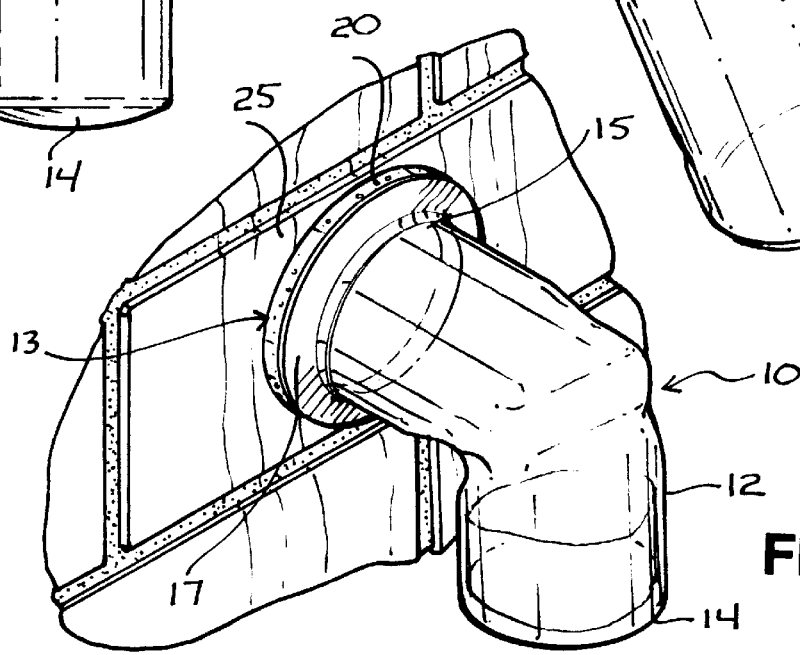
FIG. 3
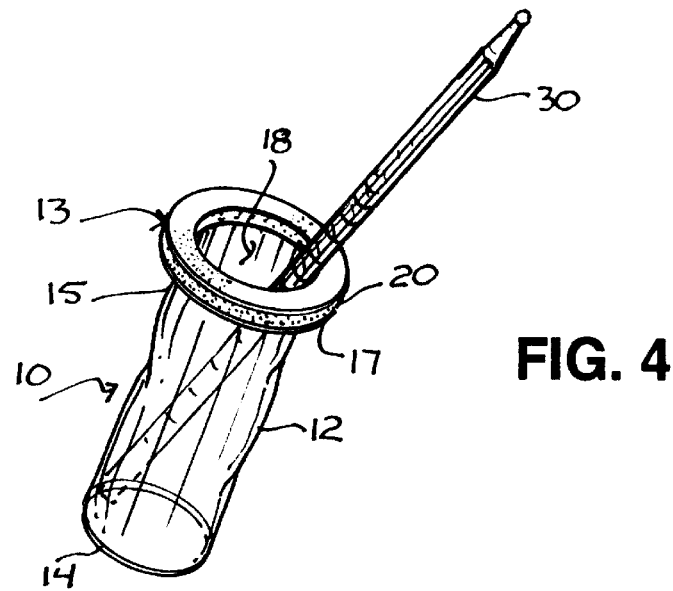
FIG. 4

METHOD AND APPARATUS FOR TESTING SURFACES

This application claims the benefit of Provisional Application Serial No. 60/078,293, filed Mar. 17, 1998.

FIELD OF THE INVENTION

The present invention pertains to testing surfaces in the field.

More specifically, the present invention concerns methods and systems for testing surfaces for soluble salts prior to applying a protective coating.

THE PRIOR ART

During preparation of surfaces prior to application of protective coatings, testing of the surfaces for soluble salt contamination is extremely important. Testing of surfaces for soluble salt contamination is typically broken down into two aspects, laboratory testing and field testing. Both laboratory testing and field testing involved a two-step procedure. The first step is to extract the salts from the substrate into a solution where they may be measured. The second step is to actually measure the ions in the solution after they have been extracted from the substrate.

Typically, to extract soluble salts from the surface of a substrate, three methods, boiling, swabbing, and the Bresle patch, are currently used. The boiling method involves taking a substrate sample, usually steel, into the laboratory, placing it in distilled or de-ionized water and boiling it for a period of one hour. Care must be taken that all instruments, measuring devices and containers are cleaned and uncontaminated, either from prior use or tap water. Rubber or latex gloves are also recommended to prevent contaminating samples or equipment with salts from the hands. This method, of course, cannot be utilized in the field.

The swab method involves taping off an appropriate sized area, and swabbing it with an appropriate quantity of distilled or de-ionized water. Cotton balls are then wetted with a pre-measured swabbing water and manually scrubbed over the taped off area. After a specific time of scrubbing, additional dry cotton balls are used to absorb the solution and return it to the working container. The solution, including all the cotton balls used, is then stirred for approximately two minutes. The extract solution is now ready for measurement. The difficulty with this method, is maintaining an uncontaminated state. In order to obtain fairly accurate measurements, sterile cotton balls must be employed and used with sterile tweezers while wearing latex gloves. Furthermore, this process is difficult to employ without losing the solution, specifically on vertical or overhead surfaces.

The final method is the Bresle patch, which is an adhesive patch with a blister in the center. The patch is placed over the surface of the substrate to be tested, and a user injects a manually measured volume of a solution with a needle and syringe. The fluid can then be manually manipulated to wash the surface. The solution is then extracted using the needle and syringe, and measured for soluble salt content. In this method, care must be taken to insure that the syringe is cleaned of all contaminants. Furthermore, the step of manually measuring the solution often gives rise to error.

Thus, the Prior Art provides methods which, while effective, include problems with contamination, inaccurate measurements of area and liquid, and testing of vertical and overhead surfaces as well as requiring a great many accessories for operation.

It would be highly advantageous, therefore, to remedy the foregoing and other deficiencies inherent in the prior art.

Accordingly, it is an object of the present invention to provide a test sleeve which can be employed on any surface regardless of orientation.

Another object of the present invention to provide a test sleeve which is inexpensive.

And another object of the present invention to provide a test sleeve which is easy to use.

Still another object of the present invention to provide a method of testing surface which is simple and effective.

Yet another object of the present invention is to eliminate cross contamination caused by reuse of materials such as syringes or working containers or physical contact.

SUMMARY OF THE INVENTION

Briefly, to achieve the desired objects of the present invention in accordance with a preferred embodiment thereof, provided is a testing sleeve for use in determining the level of soluble salts on a substrate. The testing sleeve includes a generally tubular body having a closed end and an open end. The open end includes a flange defining an aperture. An attachment member is coupled to the flange for removably securing the testing sleeve to a substrate. The aperture defined by the flange has an area of predetermined size, and, in a specific embodiment, the flange is sufficiently rigid to prevent variation in the predetermined size of the area of the aperture.

In another embodiment, a test kit for testing substrates for soluble salts including a test sleeve, a pre-measured volume of solvent solution, and a soluble salt measuring device is provided. The test sleeve includes a generally tubular body with a closed end and an open end. The open end includes a flange defining an aperture, and an attachment member coupled to the flange for removably securing the testing sleeve to a substrate.

Also provided is a method of testing a substrate for soluble salts. The method includes, providing a testing sleeve including a flexible, generally tubular body having a closed end and an open end, the open end having a flange defining an aperture, and an attachment member coupled to the flange for removably securing the testing sleeve to a substrate. Providing a solvent solution, and pouring a measured volume of the solvent solution into the testing sleeve. The testing sleeve is then affixed to a surface of a substrate to be tested. The salts on the surface of the substrate to be tested are dissolved into the solvent solution, and the testing sleeve is removed from the substrate to be tested. The amount of soluble salts contained in the solvent solution is then measured.

BRIEF DESCRIPTION OF THE DRAWINGS

The foregoing and further and more specific objects and advantages of the present invention will become readily apparent to those skilled in the art from the following detailed description of a preferred embodiment thereof taken in conjunction with the drawings, in which:

FIG. 1 is a side view of a testing sleeve in accordance with the present invention;

FIG. 2 is a perspective view of the sleeve of FIG. 1 with the protective covering partially removed from the adhesive layer;

FIG. 3 is a perspective view illustrating a testing sleeve fixed to a surface for testing;

FIG. 4 is a perspective view of a sample collected from a surface in a testing sleeve being analyzed;

DETAILED DESCRIPTION OF THE PREFERRED EMBODIMENT

Figure 5:
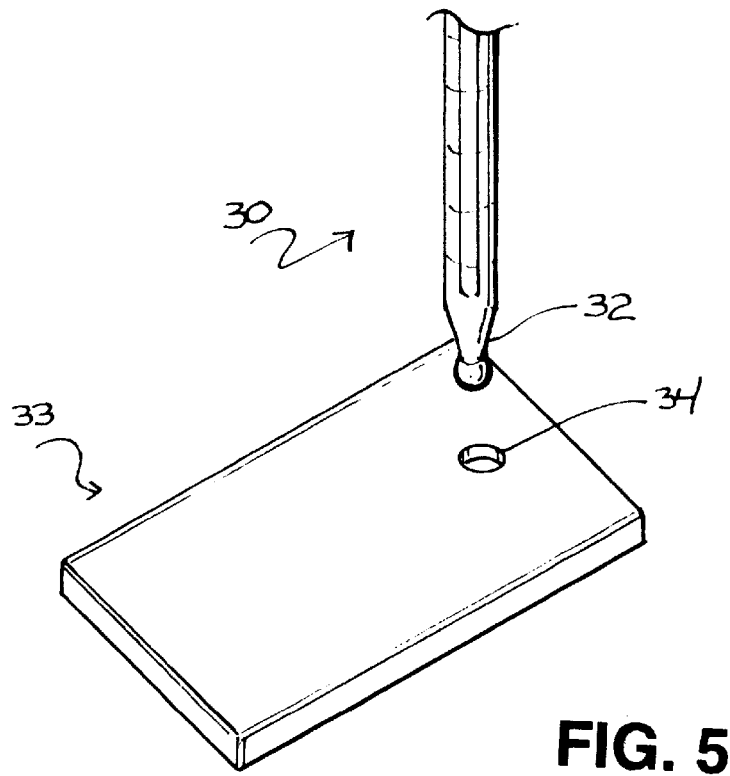
FIG. 5 is a perspective view illustrating a closed end of a titration tube and a tool for snapping off the end, according to the present invention.

Turning now to the drawings in which like reference characters indicate corresponding elements throughout the several views, attention is first directed to FIGS. 1 and 2 which illustrate a test sleeve generally designated 10 having a generally tubular body 12 and an attachment member 13 coupled thereto. Tubular body 12 is preferably formed of a flexible material, such as latex, and includes a closed end 14 and an open end 15. Open end 15 includes a flange 17 extending radially outwardly therefrom and has an aperture 18 encompassed and defined by flange 17.

Due to the thinness and flexibility of tubular body 12, the size of the area of aperture 18 can be inadvertently varied by stretching, flexing, etc. Any change in the size of the area of aperture 18 can be detrimental to the accuracy of the test as will be described in more detail below. Therefore, attachment member 13, in this specific embodiment, includes a gasket 20 coupled to flange 17. Gasket 20 helps maintain the desired area of aperture 18 and provides increased rigidity and form to open end 15 while retaining sufficient flexibility to contour to uneven surfaces. While in the preferred embodiment gasket 20 is fixed to flange 17 by an adhesive, other methods may be employed, such as heat sealing, etc. Furthermore, while a gasket is employed in this specific embodiment, it will be understood that gasket 20 can be omitted with a corresponding increase in the thickness of flange 17.

Still referring to FIGS. 1 and 2, attachment member 13 further includes an adhesive 22 carried by gasket 20. Adhesive 22 is covered by a protective sheet 23 which is peeled off prior to use. If, as stated previously, no gasket is employed, adhesive 22 is carried by flange 17.

Soluble salts, like chlorides and sulfates, are found on surfaces everywhere. These soluble salts pull moisture from the ambient environment, causing protective coatings to fail. They can also cause degradation of the substrate whether its metal, concrete, brick etc. To determine the level of contamination, a solution is applied to an area of a surface of a substrate to collect a sample of the soluble salts present. The level of contamination is typically measured in micrograms per square centimeter which is calculated by multiplying parts per million of the soluble salt by the milliliters of solution used and dividing by the surface area washed. Water is conventionally employed for the test, but in the present embodiment, the solution employed is preferably a dilution of CHLOR*RID™, soluble salt removal solution, U.S. Pat. No. 5,609,692 incorporated by reference herein.

Turning now to FIG. 3, to test a surface for soluble salt contaminates a pre-measured dose of a solution, 10 ml in this example, is inserted into test sleeve 10 such as by pouring from a pre-measured container (not shown). Protective sheet 23 is removed, and sleeve 10 is fixed to a surface 25 by adhesive 22. The area of aperture 18 determines the area of surface 25 being tested. In this embodiment, aperture 18 has an area of approximately 10cm². As can be seen, body 12 of test sleeve 10 is of sufficient length to permit a fold to be formed intermediate ends 14 and 15. The most desirable length has been found to be approximately 3–4 inches. Thus, the solution is trapped proximate closed end 14 while open end 15 is fixed to surface 25, preventing loss of solution. In this example surface 25 is vertical. However, because body 12 can be folded to lock the solution into closed end 14, a surface having any orientation, horizontal, inverted, angled, etc. can be tested.

After adhesion to surface 25, body 12 is manipulated to introduced the solution against surface 25. A collection period includes a slight massaging action by the testing individual against tubular body 12 to thoroughly wash surface 25 with the solution. The collection period is preferably two minutes in duration. When testing vertical or overhead surfaces, upon release of test sleeve 10 the solution will drain to closed end 14, allowing removal of sleeve 10 from surface 25 without loss of solution. For surfaces requiring inversion of test sleeve 10, solution can be squeezed back toward closed end 14 by compression of body 12, and retained there by introduction of a fold in body 12.

After removal of test sleeve 10 from surface 25, a titrator tube 30 is inserted through aperture 18 into the solution containing the sample of soluble salt contaminates. A reading is taken after a period of approximately one to two minutes during which the solution wicks up to the top of the titrator tube. A titrator tube is calibrated to measure parts per million of the soluble salt in solution. This is indicated by a color change, generally from pink (normal) to white (chloride level). While the number on the titrator tube next to the color change indicates parts per million, due to the surface area of aperture 18 and the pre-measured volume of solution, parts per million and micrograms per square centimeter have a one to one ratio. Thus the requirement for calculations is avoided. After use, testing sleeve 10 and titrator tube 30 are discarded to prevent contamination of subsequent tests due to remaining residues. It will be understood that other measuring devices may be employed.

Figure 6:
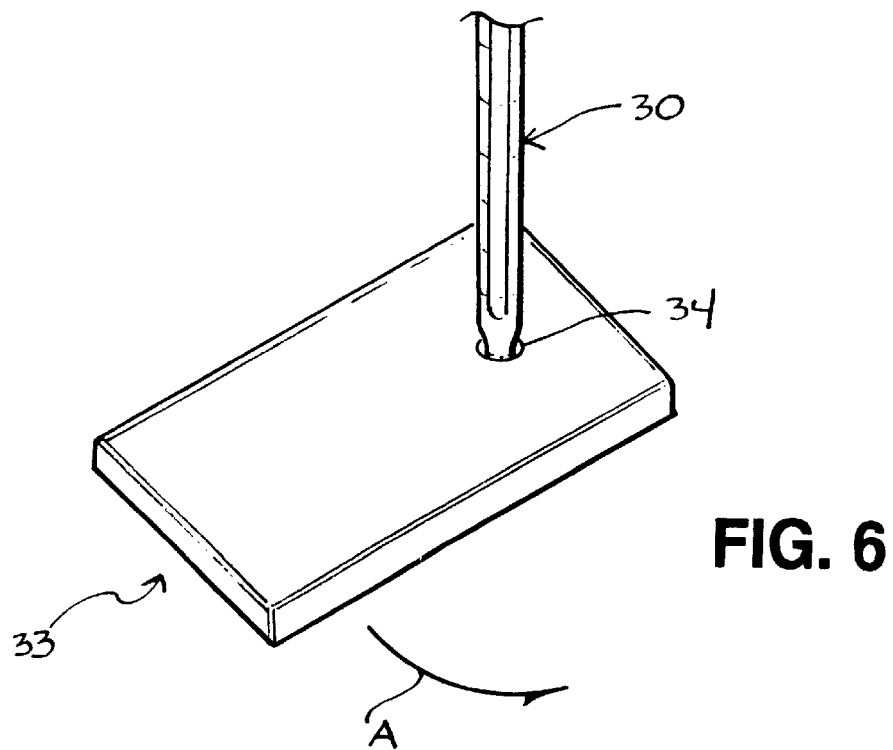
FIG. 6 is a view, illustrating the use of the tool for snapping off a sealed end of the titration tube.

Turning now to FIG. 5, titrator tube 30 preferably includes sealed ends 32, one of which is illustrated. By providing sealed ends 32, contamination is reduced prior to use. Also provided is a tool 33 which is a generally planar member having an aperture 34 formed therethrough proximate an end. To test a solution, end 32 of titrator tube 30 is inserted through aperture 34 as illustrated in FIG. 6. Tool 33 is then moved in the direction of arrowed line A to snap off end 32, unsealing titrator tube 30. The action is repeated for the opposing end, not shown. Sealed end 32 is tapered to a general point, and the aperture is sized to receive the taper, but not the full size of the titration tube. Thus the end is inserted to the fullest through aperture and cannot be inserted too far.

Various changes and modifications to the embodiments herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. A test kit for testing substrates for soluble salts comprising:

a test sleeve including a generally tubular body having a closed end and an open end, the open end having a flange defining an aperture, and an attachment member coupled to the flange for removably securing the testing sleeve to a substrate;

a pre-measured volume of solvent solution; and a soluble salt measuring device.

2. A test kit as claimed in claim 1 wherein the soluble salt measuring device includes a titrator tube.

3. A test kit as claimed in claim 1 wherein aperture of the test sleeve has an area of predetermined size, corresponding to the pre-measured volume of solvent solution, and the flange is sufficiently rigid to prevent variation in the predetermined size of the area of the aperture.

4. A test kit as claimed in claim 3 wherein the attachment member includes an adhesive carried by the flange and a protective sheet covering the adhesive.

5. A method of testing a substrate for soluble salts comprising the steps of:

providing a testing sleeve including a flexible, generally tubular body having a closed end and an open end, the open end having a flange defining an aperture, and an attachment member coupled to the flange for removably securing the testing sleeve to a substrate;

providing a solvent solution;

pouring a measured volume of the solvent solution into the testing sleeve;

affixing the testing sleeve to a surface of a substrate to be tested with the attachment member;

dissolving the salts on the surface of the substrate to be tested into the solvent solution;

removing the testing sleeve from the substrate to be tested; and measuring the amount of soluble salts contained in the solvent solution.

6. A method as claimed in claim 5 wherein the step of affixing further includes the steps of:

providing the testing sleeve with the attachment member including an adhesive carried by the flange and a protective sheet covering the adhesive;

removing the protective sheet to expose the adhesive; and applying the adhesive carried by the flange to the surface of the substrate to be tested, affixing the flange to the surface.

7. A method as claimed in claim 5 wherein the step of removing the testing sleeve includes forcing the solution to the closed end of the testing sleeve and capturing the solution at the closed end by folding the testing sleeve.

8. A method as claimed in claim 5 wherein the step of dissolving the soluble salts include forcing the solvent solution over the surface of the substrate to be tested.

9. A method as claimed in claim 8 wherein the step of forcing includes manually distorting the generally tubular body to move the solution over the surface.

10. A testing sleeve for determining the level of soluble salts on a substrate, the testing sleeve comprising:

a generally tubular body including a closed end and an open end, the open end having a flange defining an aperture having a fixed area of predetermined size and being sufficiently rigid to prevent variation in the predetermined size of the fixed area; and an attachment member including an adhesive carrier whereby a gasket is intermediate the adhesive carrier and the flange for removable securing the testing sleeve to a substrate;

whereby the fixed area of the aperture is not variable and determines the area of the substrate to be tested.

11. A testing sleeve as claimed in claim 10 wherein the tubular body is flexible.

* * * * *